(12) United States Patent
Danziger

(10) Patent No.: US 10,123,496 B1
(45) Date of Patent: Nov. 13, 2018

(54) *LEPIDIUM* PLANT NAMED 'DLEPVERGI'

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/804,664

(22) Filed: Nov. 6, 2017

(51) Int. Cl.
*A01H 5/04* (2018.01)
*A01H 5/02* (2018.01)
*A01H 6/20* (2018.01)

(52) U.S. Cl.
CPC .............. *A01H 5/04* (2013.01); *A01H 5/02* (2013.01); *A01H 6/20* (2018.05)

(58) Field of Classification Search
None
See application file for complete search history.

(56) References Cited

PUBLICATIONS

Osuna et al 2006, In Vitro Cell. Dev. Biol.—Plant 42: 596-600.*

\* cited by examiner

*Primary Examiner* — David H Kruse
(74) *Attorney, Agent, or Firm* — Cassandra Bright

(57) ABSTRACT

A new and distinct *Lepidium virginicum* plant named 'DLEPVERGI' characterized by abundant production of primary lateral branches, resulting in an above average quantity of harvestable cut flower stems. The harvested cut flower stems are well suited for commercial use as bouquet and flower arrangement filler. Flowering stems are harvested somewhat later than known commercial varieties. Plants have commercial use for cut flower production.

4 Claims, 2 Drawing Sheets
(2 of 2 Drawing Sheet(s) Filed in Color)

LEPIDIUM PLANT NAMED 'DLEPVERGI'

FIELD OF THE INVENTION

The present invention relates to a new, distinct and stable variety of *Lepidium viginicum*, hereinafter referred to as 'DLEPVERGI'. The present invention relates to seeds which are the *Lepidium viginicum* 'DLEPVERGI', as well as, plants and plant parts produced by these seeds which have all of the morphological and physiological characteristics of the *Lepidium viginicum* 'DLEPVERGI'. The present invention also relates to methods for producing these seeds and plants of the *Lepidium viginicum* 'DLEPVERGI'. Furthermore, the present invention relates to a method of producing progeny *Lepidium* plants by crossing *Lepidium* 'DLEPVERGI', as either the female or seed or male or pollen parent, with another *Lepidium* plant and selecting progeny.

BACKGROUND OF THE INVENTION

The present invention relates to a new, distinct and stable variety of *Lepidium viginicum*, and hereinafter referred to by the variety denomination 'DLEPVERGI'. The new *Lepidium* 'DLEPVERGI' originated from a self-crossing made in a controlled breeding program by the inventor in March 2014, and then first flowered in December 2014, in Mishmar Hashiva, Israel. The parent is the *Lepidium viginicum* proprietary line identified by code LEV-14-16 (unpatented). This proprietary line is the sole parent, as the resulting 'DLEPVERGI' is the result of a self-crossing of this single parent variety.

*Lepidium* is a member of the Brassicaceae family. *Lepidium viginicums* is a vascular land plant, native to North America. For the most part, plants of *Lepidium virginicum* are annual or biennial, producing small or minute flowers in racemes.

To the inventor's best knowledge, there have not been significant commercial efforts to date to hybridize and produce new and interesting *Lepidium viginicum* varieties.

Over time, the inventor has trialed *Lepidium* and found it may be advantageously grown for ornamental horticultural uses. Typically, the plants are tolerant of hot, sunny conditions, and require little water.

Leaves of *Lepidium* can be sessile or stalked, normally basally occuring. *Lepidium* plants produce upright spikes of hermaphroditic flowers.

Asexual propagation of *Lepidium* can be performed by vegetative terminal cutings, however, propagation is most commonly performed by sowing seeds.

Methods for cultivation and crossing of *Lepidium* are not well known. Brief reference to the species can be found in: *Brassicaceae, Capparaceae and Cleomaceae of North America Update*, database (version 2011) Updated for ITIS by the Flora of North America Expertise Network, in connection with an update for USDA PLANTS (2007-2010), which is herein incorporated by reference.

The *Lepimedium viginicum* seeds and plants produced by this method are uniform with respect their morphological and physiological characteristics.

A need exists for a greater variety of *Lepidium* cultivars with practical and attractive ornamental features. Additionally, a need exists for additional *Lepidium viginicum* cultivars that can be easily propagated by seed, with consistent results. The new *Lepidium* 'DLEPVERGI' was developed through a controlled breeding program and exhibits unique, desirable and stable characteristics.

SUMMARY OF THE INVENTION

The present invention provides *Lepidium* plant selections that produce a high quantity of lateral branches, resulting in many harvestable stems for cut flower purposes. Flowering stems of the new variety can be used in flower bouquets as filler plant material. The large quantity of stems produced by the new variety make this invention especially useful for commercial cut flower purposes. These qualities distinguish the new cultivar from typical *Lepidium viginicum* varieties.

These and other objectives have been achieved in accordance with the present invention which provides 'DLEPVERGI' as a new *Lepidium* cultivar that is a product of a planned breeding program conducted by the inventor, Gavriel Danziger, in Moshav Mishmar Hashiva, Israel in 2014. The parent is the *Lepidium viginicum* inbred line identified by code LEV-14-16 (unpatented).

The parental cultivar has a sufficient degree of homozygosity such that the progeny of the cross are genetypically and phenotypically uniform. The new *Lepidium viginicum* 'DLEPVERGI' therefore can be produced by sexual reproduction by crossing the parent inbred line identified by the code LEV-14-16 to produce a population of progeny plants, each of which has the combination of characteristics as herein disclosed for the new *Lepidium viginicum* 'DLEPVERGI'.

Seeds which are variety 'DLEPVERGI' are produced by crossing the parental inbred line identified by the code LEV-14-16 and are to be deposited with the National Collection of Industrial Food and Marine Bacteria (NCIMB), Ferguson Building, Bucksburn, Aberdeen, Scotland , and accorded International Depository Authority Accession No. NCIMB-42892.

OBJECTS OF THE INVENTION

The present invention relates to seeds which produce *Lepidium viginicum* 'DLEPVERGI'. The present invention also relates to *Lepidium* plants, and parts thereof; having all the physiological and morphological characteristics of *Lepidium viginicum* 'DLEPVERGI'. The present invention relates to a plant produced from seeds which are *Lepidium viginicum* 'DLEPVERGI'. The present invention also relates to plant parts, such as pollen, seeds or inflorescence produced by *Lepidium viginicum* 'DLEPVERGI'.

The present invention relates to a method of producing seed which are *Lepidium viginicum* 'DLEPVERGI', by performing a self-crossing of *Lepidium viginicum* inbred line identified by code LEV-14-16 (unpatented) and harvesting seeds produced from said cross.

The present invention also relates to a method of producing plants having all the physiological and morphological characteristics of the *Lepidium viginicum* 'DLEPVERGI' comprising the steps of (a) self-crossing *Lepidium viginicum* inbred line identified by code LEV-14-16 (unpatented) (b) harvesting seeds produced from said cross; and (c) producing plants from said harvested seeds.

The present invention also relates to producing progeny plants from the cross of *Lepidium viginicum* 'DLEPVERGI', as the female or male parent, with another *Lepidium* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Lepidium viginicum* 'DLEPVERGI' showing the colors as true as is reasonably possible with colored reproductions of this type. Colors in the photographs may differ slightly from the color values cited in the detailed botanical description which accurately describes the color of 'DLEPVERGI'.

DETAILED BOTANICAL DESCRIPTION

Figure 1:
FIG. 1 shows a side view perspective of a typical flowering stem of 'DLEPVERGI', at approximately 1 day after harvest.
Figure 2:
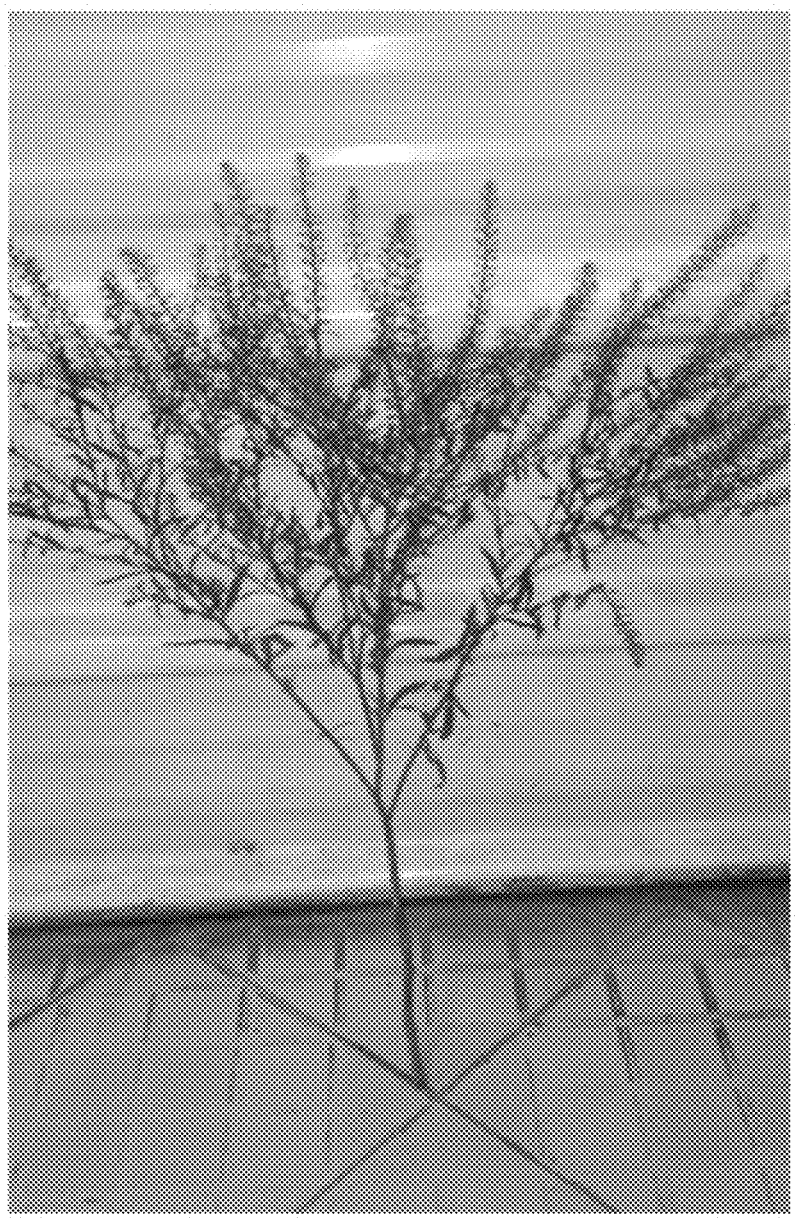
FIG. 2 shows a side view perspective of a typical flowering stem of 'DLEPVERGI', at approximately 7 days after harvest.

The present invention was created by the inventor, Gavriel Danziger during 2014, and flowered for the first time in 2014 in Mishmar Hashiva, Israel.

This invention is directed to *Lepidium* plant having all the morphological and physiological characteristics of the variety 'DLEPVERGI' produced from seeds which are the product of the self-cross of the *Lepidium viginicum* inbred line identified by code LEV-14-16 (unpatented). The parent has a sufficient degree of homozygosity such that the progeny of the cross were, and continue to be, phenotypically uniform. The new variety 'DLEPVERGI' can therefore be produced by sexual reproduction by crossing of the inbred selection identified by the code LEV-14-16 to produce a population of progeny plants, each of which has the combination of characteristics herein disclosed for the new variety 'DLEPVERGI'.

The following traits have been repeatedly observed and are determined to be unique characteristics of 'DLEPVERGI' which in combination distinguish this *Lepidium* as a new and distinct cultivar:
 1. Production of a high quantity of primary lateral branches.
 2. Late season flowering.

The commercial cultivar known to the present inventor to be the most similar in comparison to the new *Lepidium viginicum* 'DLEPVERGI' is the *Lepidium* cultivar 'Ofarim', unpatented. Plants of the new variety 'DLEPVERGI' differ from plants of 'DLEPVERGI' primarily in quantity of primary lateral branches produced. Plants of the new variety produce significantly more primary lateral branches than plants of 'Ofarim'. Foliage of the new variety is smaller and lighter green than foliage of 'Ofarim'. Plants of 'DLEPVERGI' flower later compared to plants of 'Ofarim' as well.

'DLEPVERGI' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, and branches can result depending on the growing conditions. Typically, these plants are produced outdoors, and variations in temperature and humidity can produce different results.

The aforementioned photographs, together with the following observations, measurements and values describe the new *Lepidium* 'DLEPVERGI' as grown in a greenhouse in Mishmar Hashiva, Israel, during Summer, under conditions which closely approximate those generally used in commercial practice. Plants of 'DLEPVERGI' were grown with day temperatures ranging from about 30° C. to 35° C. and night temperatures ranging from about 20° C. to 25° C. Daylength was approximately 14 hours. A shade net of 50% was used, soil was a tuff media. No artificial lighting or photoperiodic treatments were conducted.

Color references are made to the Royal Horticultural Society Colour Chart (RHS), 2005 mini edition, except where general colors of ordinary significance are used. Color values were taken under daylight conditions in a greenhouse Mishmar Hashiva, Israel . The age of the plants of 'DLEPVERGI' described is about 40 days from planting a seedling plant. The seedling plant is approximately 5 weeks old.

Botanical Classification: *Lepidium viginicum*
Parentage:
 Parent: *Lepidium viginicum* inbred line identified by code LEV-14-16 (unpatented)
Plant:
Growth Habit: Upright
Height: Approximately 60 cm during Summer, approximately 85 cm in Spring.
Plant Spread: Approximately 35 cm.
Growth Rate: Approximately 6 weeks during Summer to achieve mature flowering stage, approximately 10 weeks during Spring.
Branching Characteristics: Pseudomonopodial.
Length of Primary Lateral Branches: 25 cm in Summer, 55 cm in Spring.
Diameter of Lateral Branches: 1.5 to 2 mm.
Quantity of Primary Lateral Branches: Ranges between to 6-8 per plant.
Characteristics of Primary Lateral Branches:
 Color: Near RHS Green 138B
 Texture: Glabrous
 Strength: Strong, firm.
Internode length: Varies along the stem. In the summer— approximately 2.5 cm for the lower part of the stem, and approximately 2 cm for the upper part of the stem. In the Spring—approximately 4 cm for the lower part of the stem, and approximately 2 cm for the upper part of the stem.
Foliage:
Leaf: Most foliage is basal. Cauline leaves occur as well. The data refers to the basal leaves
 Arrangement: Rosette
 Quantity: Approximately 13 per plant in Summer. Approximately 30 per plant in Spring.
 Average Length: 11 cm.
 Average Width: 2.25 cm.
 Shape of blade: Lyrate
 Apex: Obtuse
 Base: Attenuate
 Margin: Lobed, entire.
 Texture of top surface: Scabrous
 Texture of bottom surface: Scabrous
 Appearance: top surface: Matte
 Appearance bottom surface: Matte
 Aspect: Concave
 Color:
  Young foliage upper side: Near RHS Green N137B
  Young foliage under side: Near RHS Green 137A
  Mature foliage upper side: Near RHS Green 138B
  Mature foliage under side: Near RHS Green 137C
 Venation:
  Type: Arcuate Venation color upper side: Near RHS Green 137B
Venation color under side: Near RHS Green 137C
Petiole:
    Length: Approximately 7 cm for mature foliage
    Diameter: Approximately 0.15 cm. for mature foliage
    Color: Near RHS Yellow-Green 147B
    Texture: Scabrous
Inflorescence:
Natural flowering season: Spring (February to May in Israel)
Days to flowering from a plantlet: Starting from seeds, approximately 5 weeks from planting during Summer, in Spring approximately 10 weeks.
Inflorescence and flower type and habit: The inflorescence type is a raceme and the flower type is single, the habit is upright.
Rate of flower opening: 0.5 to 2 days from bud to fully opened flower.
Flower Longevity on Plant: 0.5 to 3 days.
Persistent or Self-Cleaning: Self-Cleaning.
Vase life: Approximately 6 days.
Bud:
    Shape: Globose
    Length: Average 0.15 cm
    Diameter: Average 0.15 cm
    Color: Near RHS Yellow-Green 145A
Flower size:
    Diameter: Approx 1 mm in Summer, in Spring approx 3.5 mm.
    Length: Approx. 1 mm in Summer, in Spring approx 3 mm.
Corolla/Petals:
    Arrangement: Cruciform
    Length: 1.5 to 2 mm
    Width: 1-1.2 mm
    Quantity: 4
    Texture: Smooth
    Apex: Obtuse
    Base: Cuneate
    Shape: Oval
    Margin: Entire
    Aspect: Concave
    Color: When opening:
        Upper surface: Near RHS White 155C
        Lower surface: Near RHS White 155C
    Fully opened:
        Upper surface: Near RHS White 155C
        Lower surface: Near RHS White 155C
    Aging:
        Upper surface: Near RHS White 155C
        Lower surface: Near RHS White 155C
Calyx/Sepals:
    Quantity per flower: 4
    Shape: Orbicular
    Length: 0.5-0.7 mm
    Width: 0.4-0.6 mm
    Apex: Obtuse
    Base: Cuneate
    Margin: Entire
    Texture: Smooth
    Color: Upper Surface: Near RHS Yellow-Green 146B
        Lower Surface: Near RHS Yellow-Green 146B
Peduncle:
    Length: Average range 3 to 18 cm.
    Diameter: Approximately 1 mm.
    Color: Near RHS Green 137C
    Orientation: Upright
    Texture: Smooth
Pedicel:
    Length: Approximately 3 to 5 mm
    Diameter: Approximately 0.5 mm
    Color: Near RHS Green 137B
    Orientation: Horizontal
    Texture: Smooth
Fragrance: Not fragrant
Reproductive Organs:
Stamens:
    Number: 2
    Filament length: Approximately 1 mm.
Anthers:
    Shape: Orbicular
    Length: Approximately 0.1-0.2 mm.
    Color: Near RHS Yellow-White 151C
Pistil:
    Style:
    Number: 1
        Length: Approximately 1 mm.
        Color: Near RHS Green 143B
    Stigma:
        Shape: Two lobed
        Color: Near RHS White 155A
        Ovary Color: Near RHS Green 143B
Temperature tolerance: Tolerates a range from approximately 8° C. to 40° C.
    Seeds/Fruit:
Fruits
    Shape: Heart-shaped.
    Length: Approximately 2 to 3 mm.
    Width: Approximately 2.2 to 3 mm
    Texture: Smooth
Seeds
    Shape: Napiform
    Length: 2 mm
    Width: 1 mm.
Disease/Pest Resistance and Susceptibility: Neither resistance nor susceptibility to normal diseases and pests of *Lepidium* observed.

I claim:

1. A *Lepidium* plant named 'DLEPVERGI', representative seed deposited at the National Collection of Industrial Food and Marine Bacteria(NCIMB), Aberdeen, Scotland, having Accession Number 42892.

2. A *Lepidium* seed that produces the plant of claim 1.

3. A plant part obtained from the *Lepidium* plant of claim 1.

4. A method for producing a *Lepidium* progeny hybrid plant comprising the steps of (a) crossing *Lepidium* 'DLEPVERGI', produced from representative seed deposited with the National Collection of Industrial Food and Marine Bacteria (NCIMB), Aberdeen, Scotland, having Accession Number 42892 as a female or male parent with another *Lepidium* plant, and (b) selecting progeny.

* * * * *

UNITED STATES PATENT AND TRADEMARK OFFICE
CERTIFICATE OF CORRECTION

| | | |
|---|---|---|
| PATENT NO. | : 10,123,496 B1 | |
| APPLICATION NO. | : 15/804664 | |
| DATED | : November 13, 2018 | |
| INVENTOR(S) | : Gavriel Danziger | |

It is certified that error appears in the above-identified patent and that said Letters Patent is hereby corrected as shown below:

On the Title Page

ABSTRACT. Line 7 should read:
some what earlier than known commercial varieties. Plants In the Specification Column 2, Line 9 should read:
filler plant material. The large quantity of lateral branches produced by Column 2, Line 12 should read:
the new cultivar from typical Lepidium virgunicum varieties.

Column 3, Line 51 should read:
'DLEPVERGI' flower earlier compared to plants of 'Ofarim'

Column 3, Line 41 should read:
2. Early season flowering

Column 4, Line 51 should read:
Average Width: 4.25 cm

Signed and Sealed this
Fourth Day of October, 2022

Katherine Kelly Vidal
*Director of the United States Patent and Trademark Office*